(12) United States Patent
Yamashita et al.

(10) Patent No.: US 8,207,190 B2
(45) Date of Patent: Jun. 26, 2012

(54) ENANTIOMER OF TENATOPRAZOLE AND THE USE THEREOF IN THERAPY

(75) Inventors: Setsuo Yamashita, Tokyo (JP); Kengo Ebina, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 600 days.

(21) Appl. No.: 12/359,410

(22) Filed: Jan. 26, 2009

(65) Prior Publication Data

US 2009/0163539 A1 Jun. 25, 2009

Related U.S. Application Data

(63) Continuation of application No. 10/546,485, filed as application No. PCT/JP2004/002087 on Feb. 23, 2004, now Pat. No. 7,507,746.

(30) Foreign Application Priority Data

Feb. 24, 2003  (JP) ................................. 2003-046335

(51) Int. Cl.
  *C07D 471/02* (2006.01)
  *A61K 31/4745* (2006.01)
(52) U.S. Cl. ....................... 514/303; 546/118
(58) Field of Classification Search .................. 514/303; 546/118
  See application file for complete search history.

(56) References Cited

U.S. PATENT DOCUMENTS

| 4,738,974 | A |   | 4/1988 | Brandstrom |        |
|-----------|---|---|--------|------------|--------|
| 4,808,596 | A | * | 2/1989 | Matsuishi et al. | 514/303 |
| 5,753,265 | A | * | 5/1998 | Bergstrand et al. | 424/474 |
| 5,798,120 | A | * | 8/1998 | Tomohisa et al. | 424/482 |
| 7,034,038 | B2 |  | 4/2006 | Cohen et al. |        |

FOREIGN PATENT DOCUMENTS

| CA | 2509899 A1 | 7/2004 |
| EP | 0 124 495 A2 | 11/1984 |
| EP | 0 254 588 A1 | 1/1988 |
| JP | 59-167587 A | 9/1984 |
| JP | 63-146882 A | 6/1988 |
| JP | 6-43426 B2 | 6/1994 |
| KR | 1994-0002B24 A | 4/1994 |

OTHER PUBLICATIONS

Anon et al., Drugs in R&D, 2002, vol. 3, pp. 276-277.*
Anderson et al., *Pharmacology & Therapeutics*, 108: 294-307 (2005).
Anon et al., *Drugs in R&D*, 2002, 3: 276-277 (2002).
Kakinoki et al., *Methods and Findings in Experimental and Clinical Pharmacology*, 21(3): 179-187 (1999).
Komatsu et al., *J. Org. Chem.*, 58(17): 4529-4533 (1993).
Uchiyama et al., *Journal of Pharmacy and Pharmacology*, 51(4): 457-464 (1999).
Uchiyama et al., *Methods and Findings in Experimental and Clinical Pharmacology*, 21(2): 115-122 (1999).
Balmer et al., *Journal of Chromatography A*, 660: 269-273 (1994).
Johns, Denise, *American Laboratory*, 19: 72-74, 76 (Jan. 1987).
Johns, Denise, *International Laboratory*, 17(1): 66, 68, 70-71 (Feb. 1987).
Kakinoki et al., *Methods Find. Exp. Clin. Pharmacol.*, 21(3): 179-187 (1999).
Kamiya et al., *Chromatography*, 23: 107-108 (2002).
Komatsu et al., *J. Org. Chem.*, 58: 4529-4533 (1993).
Uchiyama et al., *J. Pharm. Pharmacol.*, 51: 457-464 (1999).
Uchiyama et al., *Methods Find. Exp. Clin. Pharmacol.*, 21(2): 115-122 (1999).

* cited by examiner

*Primary Examiner* — Niloofar Rahmani
(74) *Attorney, Agent, or Firm* — Leydig, Voit & Mayer, Ltd.

(57) ABSTRACT

This invention relates to optically active substances of tenatoprazole, (+) and (−) -5-methoxy-2-{(4-methoxy-3,5-dimethyl-2-pyridyl)methyl]sulfinyl}-1H-imidazo[4,5-b]pyridine. The compound and pharmaceutical compositions thereof are useful for anti-ulcer agent.

6 Claims, No Drawings

ENANTIOMER OF TENATOPRAZOLE AND THE USE THEREOF IN THERAPY

CROSS-REFERENCE TO RELATED APPLICATIONS

This patent application is a continuation of copending U.S. patent application Ser. No. 10/546,485, filed Oct. 7, 2005, which is the U.S. national phase of International Patent Application No. PCT/JP2004/002087, filed Feb. 23, 2004.

FIELD OF THE INVENTION

The present invention concerns tenatoprazole, and more particularly an enantiomer of tenatoprazole, a method for its preparation and its use in human or veterinary therapy.

BACKGROUND ART

Tenatoprazole, or (+)-5-methoxy-2-{[(4-methoxy-3,5-dimethyl-2-pyridyl)methyl]sulfinyl}imidazo-[4,5-b]pyridine, is described in Patent No. EP 254,588. It belongs to the group of drugs considered as proton pump inhibitors, which inhibit the secretion of gastric acid and are useful in the treatment of gastric and duodenal ulcers. It can also be used to treat gastro-oesophageal reflux, digestive bleeding and dyspepsia, because of its relatively long elimination half-life, as described in the application for French patent No. FR 02.13113.

The first known derivative of this series of proton pump inhibitors was omeprazole, described in Patent No. EP 001,529, which is endowed with properties which inhibit the secretion of gastric acid and is widely employed as an anti-ulcerative in human therapeutics.

In addition to omeprazole, other proton pump inhibitors are well known, and particular mention can be made of rabeprazole, pantoprazole and lansoprazole, which all exhibit structural analogy and lansoprazole, which all exhibit structural analogy and belong to the group of pyridinyl methyl sulfinyl benzimidazoles. These compounds are sulfoxides presenting with asymmetry at the level of the sulphur atom, and therefore generally take the form of a racemic mixture of two enantiomers.

Like omeprazole and other sulfoxide with an analogue structure, tenatoprazole has an asymmetric structure and may therefore be present in the form of a racemic mixture or of its enantiomers. Thus it may exist in the form of its two enantiomers with R and S configurations, or (+) or (−), respectively.

Recent studies have shown that, unlike all the other proton pump inhibitors such as, for example, omeprazole or lansoprazole, and unexpectedly, tenatoprazole is endowed with a markedly prolonged duration of action, resulting from a plasma half-life which is about seven times longer. Thus the clinical data collected have shown that tenatoprazole enables a degree of symptom relief and healing of gastric lesions which is superior to that achieved by other drugs belonging to the same therapeutic category of proton pump inhibitors, which thus allows its effective use in the treatment of atypical and oesophageal symptoms of gastro-oesophageal reflux, digestive bleeding and dyspepsia, as indicated above.

Studies performed by the application have made it possible to show that the two enantiomers contribute differently to the properties of tenatoprazole, and that the two enantiomers, (+) and (−) exhibit significantly different pharmacokinetic properties. Thus it is possible to prepare medicinal products with specific activity by isolating the enantiomers, and these enantiomers themselves exhibit a different pharmacokinetic profile from that of the known racemic mixture. It then becomes possible to use each of these enantiomers more effectively in precise indications for the treatment of perfectly identified pathologies.

SUMMARY OF THE INVENTION

Thus the aim of the present invention is the followings:
1. The compound (−)-tenatoprazole, or (−)-5-methoxy-2-{[(4-methoxy-3,5-dimethyl-2-pyridyl)methyl]sulfinyl}imidazo-[4,5-b]pyridine, or one of its salts.
2. A method for the preparation of (−)-tenatoprazole, or (−)-5-methoxy-2-{[(4-methoxy-3,5-dimethyl-2-pyridyl)methyl]sulfinyl}imidazo-[4,5-b]pyridine, or one of its salts, comprising column chromatography on racemic mixture.
3. The method according to the above 2, wherein the column chromatography is chiral or HPLC chromatography.
4. The method according to the above 2 or 3, wherein (−)-tenatoprazole, or (−)-5-methoxy-2-{[(4-methoxy-3,5-dimethyl-2-pyridyl)methyl]sulfinyl}imidazo-[4,5-b]pyridine is salified by the action of basic mineral reagents comprising alkaline or earth-alkaline counter-ion.
5. A pharmaceutical composition comprising (−)-tenatoprazole, or (−)-5-methoxy-2-{[(4-methoxy-3,5-dimethyl-2-pyridyl)methyl]sulfinyl}imidazo-[4,5-b]pyridine, or one of its salts, and one more pharmaceutically acceptable excipients or substances.
6. The pharmaceutical composition according to the above 5, wherein (−)-tenatoprazole, or (−)-5-methoxy-2-{[(4-methoxy-3,5-dimethyl-2-pyridyl)methyl]sulfinyl}imidazo-[4,5-b]pyridine takes the form of an alikalie or earth-alkaline metal salt.
7. The pharmaceutical composition according to the above 5, wherein (−)-tenatoprazole, or (−)-5-methoxy-2-{[(4-methoxy-3,5-dimethyl-2-pyridyl)methyl]sulfinyl}imidazo-[4,5-b]pyridine takes the form of a sodium, potassium, lithium, magnesium or calcium salt.
8. The pharmaceutical composition according to the above 5 to 7, comprising unitary doses containing from about 10 to about 80 mg of active ingredient.
9. The use of (−)-tenatoprazole, or (−)-5-methoxy-2-{[(4-methoxy-3,5-dimethyl-2-pyridyl)methyl]sulfinyl}imidazo-[4,5-b]pyridine for the treatment of digestive pathologies.
10. The use of (−)-tenatoprazole, or (−)-5-methoxy-2-{[(4-methoxy-3,5-dimethyl-2-pyridyl)methyl]sulfinyl}imidazo-[4,5-b]pyridine for the treatment of digestive pathologies wherein the inhibition of acid secretion must be strong and prolonged.
11. The use of (−)-tenatoprazole, or (−)-5-methoxy-2-{[(4-methoxy-3,5-dimethyl-2-pyridyl)methyl]sulfinyl}imidazo-[4,5-b]pyridine for the treatment of Barrett's syndrome, atypical and oesophageal symptoms of gastro-oesophageal reflux, and digestive bleeding refraxtory to other proton pump inhibitors.
12. The use of (−)-tenatoprazole, or (−)-5-methoxy-2-{[(4-methoxy-3,5-dimethyl-2-pyridyl)methyl]sulfinyl}imidazo-[4,5-b]pyridine for the treatment of digestive pathologies, gastro-oesophageal reflux, and digestive bleeding, in patients receiving multiple drug therapy.
13. The use of (−)-tenatoprazole, or (−)-5-methoxy-2-{[(4-methoxy-3,5-dimethyl-2-pyridyl)methyl]sulfinyl}imidazo-[4,5-b]pyridine in combination with one of more antibiotics in the manufacture of a medicinal product for the treatment of duodenal ulcer resulting from an infection by *Helicobacter pylori*.

14. The use of (−)-tenatoprazole, or (−)-5-methoxy-2-{[(4-methoxy-3,5-dimethyl-2-pyridyl)methyl]sulfinyl}imidazo-[4,5-b]pyridine in the manufacture of a medicinal product displaying improved pharmacokinetic properties.

15. The compound (+)-tenatoprazole, or (+)-5-methoxy-2-{[(4-methoxy-3,5-dimethyl-2-pyridyl)methyl]sulfinyl}imidazo-[4,5-b]pyridine, or one of its salts.

16. A method for the preparation of (+)-tenatoprazole, or (+)-5-methoxy-2-{[(4-methoxy-3,5-dimethyl-2-pyridyl)methyl]sulfinyl}imidazo-[4,5-b]pyridine, or one of its salts, comprising that chloroform is used as a solvent and 5-methoxy-2-[[(4-methoxy-3,5-dimethyl-2-pyridyl)methyl]thio]imidazo-[4,5-b]pyridine is subjected to asymmetric oxidation.

17. The method according to the above 16, wherein optically active binaphthol, titanium tetraisopropoxide, water and tert-buthylhydroperoxide are used.

18. A pharmaceutical composition comprising (+)-tenatoprazole, or (+)-5-methoxy-2-{[(4-methoxy-3,5-dimethyl-2-pyridyl)methyl]sulfinyl}imidazo-[4,5-b]pyridine, or one of its salts, and one more pharmaceutically acceptable excipients or substances.

19. The pharmaceutical composition according to the above 18, wherein (+)-tenatoprazole, or (+)-5-methoxy-2-{[(4-methoxy-3,5-dimethyl-2-pyridyl)methyl]sulfinyl}imidazo-[4,5-b]pyridine takes the form of an alikalie or earth-alkaline metal salt.

20. The pharmaceutical composition according to the above 18, wherein (+)-tenatoprazole, or (+)-5-methoxy-2-{[(4-methoxy-3,5-dimethyl-2-pyridyl)methyl]sulfinyl}imidazo-[4,5-b]pyridine takes the form of a sodium, potassium, lithium, magnesium or calcium salt.

21. The use of (+)-tenatoprazole, or (+)-5-methoxy-2-{[(4-methoxy-3,5-dimethyl-2-pyridyl)methyl]sulfinyl}imidazo-[4,5-b]pyridine, or one of its salts for the treatment of digestive pathologies.

22. The use of (+)-tenatoprazole, or (+)-5-methoxy-2-{[(4-methoxy-3,5-dimethyl-2-pyridyl)methyl]sulfinyl}imidazo-[4,5-b]pyridine for the treatment of Barrett's syndrome, atypical and oesophageal symptoms of gastro-oesophageal reflux, and digestive bleeding refraxtory to other proton pump inhibitors.

23. The use of (+)-tenatoprazole, or (+)-5-methoxy-2-{[(4-methoxy-3,5-dimethyl-2-pyridyl)methyl]sulfinyl}imidazo-[4,5-b]pyridine for the treatment of digestive pathologies, gastro-oesophageal reflux, and digestive bleeding, in patients receiving multiple drug therapy.

BEST MODE FOR CARRYING OUT THE INVENTION

The (−) enantiomer of tenetoprazole can be used in the form of a salt, including an alkaline or earth-alkaline metal salt, and, for example, in the form of a sodium, potassium, lithium, magnesium or calcium salt. These salts can be obtained from the (−) enantiomer of tenatoprazole which has previously been isolated by salification, according to the standard method of the technique, for example by the action of basic mineral reagents comprising alkaline or earth-alkaline counter-ions.

The (−) enantiomer complying with the present invention can be obtained in a pure optical form simply from the racemic mixture, using any appropriate method of separation, and more particularly by preparative column chromatography, for example, chiral or HPLC chromatography. "Pure optical form" implies that the (−) enantiomer is substantially exempt of the (+) enantiomer, or only contains traces of it. If relevant, salification with a base is then performed in an appropriate solvent, to form a salt, and particularly an alkaline or earth-alkaline metal salt.

The principle of the chiral chromatography method is based on the difference in affinity existing between the (+) and (−) enantiomers and the chiral selector of the stationary phase. This method enables the separation of enantiomers with a satisfactory yield.

The (−) enantiomer of tenatoprazole corresponds to (−)-5-methoxy-2-{[(4-methoxy-3,5-dimethyl-2-pyridyl)methyl]sulfinyl}imidazo-[4,5-b]pyridine, or (−)-tenatoprazole. This form can be determines by optical rotation measurements using standard technique.

For example, it is possible to prepare a solution of the desired enantiomer at 0.25% (50 mg of a sample per 20 ml of solvent) dissolved in DMF or acetonitrile, and using a polarimeter of a commonly employed type (Jobin Yvon). Thus, the angle of optical rotation of (−)-tenatoprazole is laevogyre in dimethylformamide and acetonitrile, and its melting point is 130° C. (decomposition).

The racemic mixture used as the starting material can be obtained using known processes, for example according to the procedure described in Pat. No. EP 254,588. Thus, it can be prepared using an oxidising agent, such as perbenzoic acid, to treat the corresponding sulfide arising from the condensation of a thiol and a pyridine, preferably in the presence of a base such as potassium hydroxide in an appropriate solvent, for example, ethanol, under heating.

The method used to separate enantiomers from the racemic mixture by high performance liquid chromatography (HPLC) makes it possible to isolate the (−) enantiomer with excellent purity (chiral purity: min. 98.8% of the surface area).

Unexpectedly, studies performed on the enantiomer prepared as above have demonstrated that it is endowed with pharmacokinetic properties which are fundamentally different from those of standard proton pump inhibitors, and of racemic tenatoprazole, thus suggesting that it could be used in specific indications.

Thus the racemic mixture and the (−) isomer of tenatoprazole differ significantly in terms of their pharmacokinetic properties, as shown by the studies described below. This characteristic is essential, as it will allow the availability to clinicians of a medicinal product specifically adapted to the effective treatment of determined pathologies.

More particularly, the different pharmacokinetic parameters displayed, and notably the $AUC_{0-inf}$ (area under the curve) and $t_{1/2}$ (elimination half-life), some subjects were genotyped in order to identify the type of metaboliser, slow or rapid, to which they belonged.

In parallel, a chiral pharmacokinetic study was conducted to assess the preponderance of the pharmacokinetic characteristics of the (−) isomer in the pharmacokinetics of racemic tenatoprazole.

As a general rule, the main problem encountered regarding the metabolism of proton pump inhibitors is that they are mostly metabolised by cytochrome 2C19, which is controlled by chromosome 10, and they thus exhibit genetic polymorphism, i.e. activity which varies as a function of the type of patient population. This results in variable plasma levels and susceptibility to possibly harmful drug interactions, depending on the individuals concerned.

It seems clear that homozygote subjects with a mutation on exon 5, giving rise to the CYP2C19*2/*2 genotype, exhibit pharmacokinetic characteristics which differ totally from those seen in the standard population. These subjects have a very weak metabolic activity concerning CYP2C19, which is responsible for the metabolism of tenatoprazole. Analysis of the plasma after chiral separation has shown that these these subjects displayed a highly significant increase in the (+) isomer when compared with the (−) isomer. These subjects are qualified as slow metabolisers.

Conversely, subjects who are rapid metabolisers, characterised by the CYP2C19*1/*1 genotype, display a higher concentration of the (−) isomer than of the (+) isomer.

Thus, the (+) isomer is metabolised via one preponderant pathway, CYP2C19, while the (−) isomer is metabolised by two pathways, i.e. CYP2C19 and CYP3A4.

These observations have led to the proposal of isolating and administering a single isomer, the (−) isomer, which would have the following advantages:

- a reduction in between-subject variations, hense a better use of the product and a more homogenous response to treatment in all patients,
- improved impregnation of the product, because the rate of elimination is slower and the mean residence time in the body (MRT) is longer,
- a reduction in the number of drug interactions with potentially concomitant medications. Indeed, the (−) isomer is metabolised via two pathways, cytochromes 2C19 and 3A4, which can compensate for any deficiency or blockade of cytochrome 2C19,
- ease of use in all types of patients, whether they are slow or rapid metabolisers. Indeed, the (−) isomer in a slow metaboliser will be metabolised by CYP3A4, thus making it possible to achieve uniform pharmacokinetic parameters whatever the patients, whether they are slow or rapid metabolisers. Furthermore, isolation of the (−) enantiomer has made it possible to determine a pharmacokinetic profile which differs from that of the racemic mixture, and notably a mean plasma half-life of between about 10 and 12 hours for the (−) enantiomer, at doses of between 20 mg and 80 mg. In contrast, the racemic compound is endowed with a mean plasma half-life of approximately 7 hours at a dose of 20 mg and 9 hours at a dose of 80 mg.

These significantly different properties, in addition to the pharmacological properties found with the racemic mixture, and well known for the pharmaco-therapeutic category of proton pump inhibitors (and notably the inhibitory activity of H+-K+-ATPase pumps on gastric secretion), show that the (−) enantiomer of tenatoprazole can be used to advantage in the treatment of digestive pathologies where it is necessary to obtain a strong and prolonged inhibition of acid secretion. This is the case in Barrett's syndrome, which causes pre-cancerous damage linked to garsro-oesophageal reflux, where the risk of oesophageal adenocarcinoma is directly proportional to the incidence, severity and duration of gastro-oesophageal reflux episodes.

The (−) enantiomer of tenatoprazole is also suitable for the treatment of Zollinger-Ellison syndrome and other syndromes involving acid hypersecretion, the treatment of atypical and oesopageal symptoms of gastro-oesophageal reflux, digestive bleeding refractory to other proton pump inhibitors and treatment of these diseases in patients receiving multiple drug therapy, particularly those receiving treatment which involved the administration of several drugs, and especially elderly patients, with the aim of preventing incidents associated with a drug interaction.

The (−) enantiomer of tenatoprazole can also be used, preferably in combination with one or more antibiotics, to treat ulcers in the event of *Helicobacter pylori* infection, and notably to eradicate *Helicobacter pylori* to favour healing of the duodenal ulcer and prevent any recurrence.

The (−) enantiomer of tenatoprazole, in the treatment of the pathologies listed above, and most particularly in the treatment of Barrett's and Zollinger-Ellison syndromes and of gastro-oesophageal reflux and digestive bleeding, can be administered in standard forms adapted to the method of administration chosen, for example via the oral parenteral routes, and preferably via the oral or intravenous routes.

For example, it is possible to use tablet or capsule formulations containing the (−) enantiomer of tenatoprazole as the active substance, or oral solution or emulsions or solutions for parenteral administration containing a tenatoprazole can be chosen, for example, from amongst sodium, potassium, lithium, magnesium or calcium salts.

As an example, an appropriate formulation for tablets containing 20 mg of the (−) isomer of tenatoprazole in combination with pharmaceutically-acceptable substrates and excipients, is shown below:

| (−) tenatoprazole | 30.0 mg |
|---|---|
| lactose | 40.0 mg |
| aluminium hydroxide | 17.5 mg |
| hydroxypropyl cellulose | 8.0 mg |
| Talc | 4.5 mg |
| titanium dioxide | 5.0 mg |
| magnesium stearate | 20. mg |
| standard excipients qs | 160.0 mg |

An example of a formulation for a size 2, gastro-resistant enteric capsule (capsule shell made of acetophtalate, polyvinylpyrrololidone derivatives and acrylic resins), containing 40 mg the (−) isomer of tenatoprazole is shown below:

| (−)-tenatoprazole | 40 mg |
|---|---|
| lactose | 200.0 mg |
| magnesium stearate | 10.0 mg |

The dosage is determined by the practitioner as a function of the patient's state and the severity of the condition. It is generally between 10 and 120 mg, and preferably between 20 and 40 mg of the (−)-enantiomer of tenatoprazole, per day. For example, it can be administered at a rate of one intake of 1 or 2 unit doses, (e.g. tablets), each containing 10 to 80 mg, and preferably 20 to 40 mg, of the active substance per day, for a period of time which can range from 4 to 12 weeks, in the context of initial or maintenance therapy. In the case of a pediatric form adapted for use in young children, for example, in the form of an oral solution, the unit dose can be lower, for example, 2 or 5 mg. In the case of severe disorders, it may be effective to administer the medicinal product in the first instance via the intravenous route, and subsequently via the oral route. The invention also has the advantage of permitting effective, sequential treatment with the administration of a single tablet containing 40 mg or 80 mg, per week.

One of the advantages of the present invention is that it allows treatment of the pathologies referred to above with a dosage limited to a single dose of medication per day, including in the treatment of duodenal ulcer resulting from *Helicobacter pylori* infection, unlike standard drugs, including standard proton pump inhibitors, which require two daily doses.

The aim of the present invention is also the (+) configuration enantiomer of the tenatoprazole and its use in human or veterinary therapeutics.

For example, the (+) enantiomer of tenatoplazole can be obtained by using chloroform, an industrially acceptable solvent, in accordance with the method proposed by Umemura et al. (J. Org. Chem. 1993, 58, 4592) as follows:

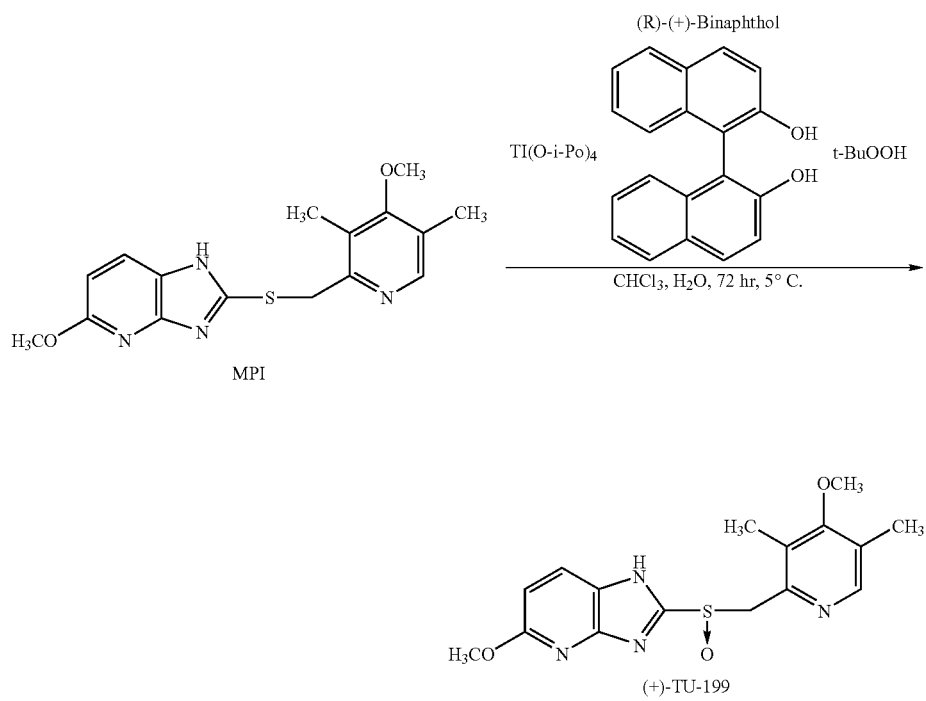

The invention provides selectivity of asymmetric oxidation at approx. 80% ee whereas the method by Uemura et al., using carbon tetrachloride as a solvent provides optically active substances at a lower purity (refer to Table 1 below).

TABLE 1

| Solvent | (+) tenatoprozole selectivity (% ee) |
| --- | --- |
| Chloroform | 82 |
| Methylene chloride | 6 |
| Carbon tetrachloride | 15 |
| THF | 14 |
| Ethyl acetate | 12 |

The method described in the invention is able to form (+)tenatoprazole by using binaphthol (R) whereas (−) tenatoprozole by using binaphthol (S).

Alkali metal salts of the (+) enantiomer of tenatoprazole of the invention, or (+-5-methoxy-2-{(4-methoxy-3,5-dimethyl-2-pyridyl)methyl]sulfinyl}-1H-imidazo[4,5-b]pyridine indicated by the structural formula include inorganic compounds such as sodium and potassium. Alkali metal salts to be used in the invention are pharmaceutical grades.

Since the compound with the foregoing structure and their alkali metal salts may be present in a form of hydrate or solvate, these hydrates and solvates are also included in the active ingredients of the invention.

The (+) enantiomer of tenatoplazole can be administered and formulated in the same ways as that of (−) enantiomer of tenatoplazole, as aforementioned.

As example of the preparation of the (−) and (+) enantiomer of tenatoprazole is described below in order to illustrate the present invention.

EXAMPLES

Example 1

(−)-5-methoxy-2-{(4-methoxy-3,5-dimethyl-2-pyridyl)methyl]sulfinyl}-1H-imidazo[4, 5-b]pyridine The conditions for preparative chromatography, shown as an example, are as follows:
Column: 265×110 mm ChiralPak®
Chiral Stationary Phase selector of the Amylose tris type [(S)-a methylbenzylcarbamate]
Flow rate: 570 ml/min
Detection: UV 240 nm
Temperature: Ambient temperature
These conditions are implemented on a liquid preparative chromatography apparatus.

Introduce approximately 2 g of the racemic mixture if tenatoprazole exhibiting purity higher than 99.5%. The (−) enantiomer is identified by measuring the angle of optical rotation, which must be laevogyre. This measurement can be performed directly on the column, the product being dissolved in the solvent (acetonitrile).

Example 2

(+)-5-methoxy-2-{(4-methoxy-3,5-dimethyl-2-pyridyl)methyl]sulfinyl}-1H-imidazo[4, 5-b]pyridine (R)-(+)-binaphthol 85 g (0.311 mol, 0.2 equivalence), ortho titanic acid isopropyl 42 g (0.148 mol, 0.1 equivalence), water 55 g (3.06 mol) and chloroform 7.5 L were stirred for 1 hour at room temperature. To the resultant, 5-methoxy-2-{(4-methoxy-3,5-dimethyl-2-pyridyl)methyl] thio}imidazo[4,5-b]pyridin e (MPI), 0.5 kg, was added and stirred for 0.5 hours at room temperature. The thus-prepared mixture was cooled to 5° C. and then 70% aqueous solution of tert-butylhydroperoxide, 0.4 L (approx. 3.0 mol, 2.0 equivalence) was added and stirred for 72 hours at the same temperature as above. After the reaction endpoint was confirmed by HPLC, an aqueous solution of sodium hydroxide was added thereto to separate the aqueous layer, thus removing foreign matter. Then, the resultant was concentrated. Ethyl acetate was added to concentrated residues, which were then heated and suspended. The thus-prepared crude crystalline substances were dissolved in water and neutralized to pH 6.8 with a diluted sulfuric acid solution which was chilled with ice. Deposited crystals were filtered, dried and recrystallized by addition of ethanol to obtain (+)-5-methoxy-2-{(4-methoxy-3,5-dimethyl-2-pyridyl)methyl]sulfinyl}-1H-imidazo[4, 5-b]pyridine {(+)-TU-199}

Yield: 77%

Optical purity: 96.6% ee

Chemical purity: 94.5%

Melting point: 135° C.

Optical rotation: +1840 (conditions: C=1.0, N,N-dimethylformaldehyde solution)

Ultraviolet absorption spectrum: (10 μg/mL)λmax (nm): 316, 273, 206

When measurements were carried out, for a solubility of (+), (−) forms and a racemic form (±) of tenatoprazole in relation to water, it was found that the (+) form dissolved almost 3 times greater than the racemic body and (−) form dissolved over 2 times greater than the racemic form, exhibiting favorable physical properties in preparing drugs (refer to Table 2 below).

TABLE 2

|  | (+) form | (−) form | (±)racemic form |
|---|---|---|---|
| Solubility (water) μg/mL | 93.0 | 74.4 | 34.6 |

The invention claimed is:

1. The compound (+)-tenatoprazole, or (+)-5-methoxy-2-{[(4-methoxy-3,5-dimethyl-2-pyridyl)methyl]sulfinyl}imidazo-[4,5-b]pyridine, or one of its salts, wherein the optical purity is at least 96.6% ee.

2. A method for the preparation of (+)-tenatoprazole, or (+)-5-methoxy-2-{[(4-methoxy-3,5-dimethyl-2-pyridyl)methyl]sulfinyl}imidazo-[4,5-b]pyridine, or one of its salts, wherein the optical purity is at least 96.6% ee, comprising subjecting 5-methoxy-2-[[(4-methoxy-3,5-dimethyl-2-pyridyl)methyl]thio]imidazo-[4,5-b]pyridine to asymmetric oxidation in the presence of chloroform.

3. The method according to claim 2, wherein the method further comprises the use of optically active binaphthol, titanium tetraisopropoxide, water and tert-buthylhydroperoxide.

4. A pharmaceutical composition comprising (+)-tenatoprazole, or (+)-5-methoxy-2-{[(4-methoxy-3,5-dimethyl-2-pyridyl)methyl]sulfinyl}imidazo-[4,5-b]pyridine, or one of its salts with an optical purity of at least 96.6% ee, and one more pharmaceutically acceptable excipients or substances.

5. The pharmaceutical composition according to claim 4, wherein (+)-tenatoprazole, or (+)-5-methoxy-2-{[(4-methoxy-3,5-dimethyl-2-pyridyl) methyl]sulfinyl}imidazo-[4,5-b]pyridine is in the form of an alkaline or earth-alkaline metal salt.

6. The pharmaceutical composition according to claim 4, wherein (+)-tenatoprazole, or (+)-5-methoxy-2- {[(4-methoxy-3,5-dimethyl-2-pyridyl)methyl]sulfinyl}imidazo-[4,5-b]pyridine is in the form of a sodium, potassium, lithium, magnesium or calcium salt.

* * * * *